(12) United States Patent
Bessen et al.

(10) Patent No.: US 9,964,529 B2
(45) Date of Patent: May 8, 2018

(54) METHOD FOR CHECKING THE FUNCTION OF A SENSOR FOR DETECTING PARTICLES, AND A SENSOR FOR DETECTING PARTICLES

(71) Applicant: Robert Bosch GmbH, Stuttgart (DE)

(72) Inventors: Michael Bessen, Stuttgart (DE); Karola Herweg, Stuttgart (DE); Mathias Klenk, Tuebingen (DE); Benjamin Gaertner, Neureut (DE)

(73) Assignee: ROBERT BOSCH GMBH, Stuttgart (DE)

( * ) Notice: Subject to any disclaimer, the term of this patent is extended or adjusted under 35 U.S.C. 154(b) by 79 days.

(21) Appl. No.: 14/409,129

(22) PCT Filed: Jun. 12, 2013

(86) PCT No.: PCT/EP2013/062151
§ 371 (c)(1),
(2) Date: Dec. 18, 2014

(87) PCT Pub. No.: WO2013/189806
PCT Pub. Date: Dec. 27, 2013

(65) Prior Publication Data
US 2015/0177204 A1     Jun. 25, 2015

(30) Foreign Application Priority Data
Jun. 21, 2012   (DE) .................. 10 2012 210 525

(51) Int. Cl.
*F01N 11/00* (2006.01)
*G01N 33/00* (2006.01)
(Continued)

(52) U.S. Cl.
CPC ..... *G01N 33/0006* (2013.01); *F02D 41/1466* (2013.01); *F02D 41/1494* (2013.01);
(Continued)

(58) Field of Classification Search
CPC ............ G01N 33/0006; G01N 33/007; G01N 27/4163; G01N 27/4175; G01N 15/0606;
(Continued)

(56) References Cited

U.S. PATENT DOCUMENTS

| 7,411,514 B2 | 8/2008 | Enomoto |
| 7,872,480 B2 * | 1/2011 | Kato ................. G01N 27/4065 204/406 |

(Continued)

FOREIGN PATENT DOCUMENTS

| CN | 1766664 A | 5/2006 |
| CN | 101813494 A | 8/2010 |

(Continued)

OTHER PUBLICATIONS

Machine translation JP2011080439A.*
International Search Report for PCT/EP2013/062151, dated Jun. 12, 2013.

*Primary Examiner* — Helen Kwok
*Assistant Examiner* — Nashmiya Fayyaz
(74) *Attorney, Agent, or Firm* — Norton Rose Fulbright US LLP; Gerard Messina

(57) ABSTRACT

A method for checking the function of a sensor for detecting soot is provided, the sensor including at least two measuring electrodes situated on a substrate made of an electrically insulating material, and a heating element, the method including: carrying out a first current-voltage measurement at a first temperature to ascertain a first measured variable, carrying out a second current-voltage measurement at a second temperature to ascertain a second measured variable, and forming a difference between the first measured variable and the second measured variable.

25 Claims, 1 Drawing Sheet

(51) Int. Cl.
*G01N 15/06* (2006.01)
*F02D 41/14* (2006.01)
*F02D 41/22* (2006.01)
*G01M 15/10* (2006.01)
*G01N 27/04* (2006.01)
*G01R 31/02* (2006.01)
*F02D 41/20* (2006.01)

(52) U.S. Cl.
CPC ......... *F02D 41/222* (2013.01); *G01M 15/102* (2013.01); *G01N 15/0606* (2013.01); *G01N 15/0656* (2013.01); *G01N 27/04* (2013.01); *G01R 31/02* (2013.01); *F02D 2041/2086* (2013.01); *Y02T 10/40* (2013.01)

(58) Field of Classification Search
CPC ................ G01N 15/0656; G01N 27/04; F02D 41/1495; F02D 41/222; F02D 41/1466; F02D 41/1494; F02D 2041/2086; G01M 15/102; G01R 31/02; Y02T 10/40
USPC .......................................................... 73/1.06
See application file for complete search history.

(56) References Cited

U.S. PATENT DOCUMENTS

| | | |
|---|---|---|
| 8,550,708 B2 | 10/2013 | Xie et al. |
| 8,823,400 B2 * | 9/2014 | Hocken .............. F02D 41/1466 324/691 |
| 2003/0196499 A1 | 10/2003 | Bosch et al. |
| 2011/0109331 A1 | 5/2011 | Nelson et al. |
| 2011/0314899 A1 | 12/2011 | Di Miro et al. |
| 2012/0023908 A1 * | 2/2012 | Klenk ................. F02D 41/1438 60/274 |
| 2012/0031169 A1 | 2/2012 | Sakamoto et al. |
| 2012/0260636 A1 * | 10/2012 | Hashida .................. F01N 11/00 60/276 |
| 2013/0000678 A1 * | 1/2013 | Hocken .............. F02D 41/1466 134/20 |

FOREIGN PATENT DOCUMENTS

| | | | |
|---|---|---|---|
| CN | 102253086 A | | 11/2011 |
| CN | 102565559 A | | 7/2012 |
| DE | 100 59 683 | | 6/2002 |
| DE | 101 11 269 | | 9/2002 |
| DE | 101 49 333 | | 5/2003 |
| DE | 10 2005 030134 | | 1/2007 |
| DE | 10 2010 042226 | | 4/2011 |
| FR | 2 919 928 | | 2/2009 |
| JP | 2011080439 A | * | 4/2011 |
| JP | 2011080439 A | | 4/2011 |
| JP | 2012037373 | | 2/2012 |
| JP | 2012077716 A | | 4/2012 |
| WO | WO 2003/006976 | | 1/2003 |

* cited by examiner

METHOD FOR CHECKING THE FUNCTION OF A SENSOR FOR DETECTING PARTICLES, AND A SENSOR FOR DETECTING PARTICLES

BACKGROUND OF THE INVENTION

1. Field of the Invention

The present invention relates to sensors for detecting particles, in particular sooty particles in an exhaust gas flow of an internal combustion engine.

2. Description of the Related Art

It is known from practice to measure a concentration of particles in an exhaust gas, for example, sooty particles or dust particles, with the aid of two electrodes which are situated on a ceramic. This may, for example, be carried out via a measurement of the electrical resistance of the ceramic material separating the two electrodes. Such sensors are, for example, used in an exhaust gas system of an internal combustion engine, for example, an internal combustion engine of the diesel version. They are generally situated downstream from the internal combustion engine or the diesel particulate filter. Due to growing environmental awareness and partly due to legal requirements, soot emissions must be monitored in the future during the driving operation of a motor vehicle, and the functionality of this monitoring must be ensured. This type of monitoring of the functionality is generally referred to as on-board diagnostics. In addition, it is necessary to predict the load of diesel particulate filters to achieve high system reliability with few efficient fuel-saving regeneration cycles, in order to be able to use more economical filter materials such as cordierite. A resistive soot sensor provides one option for this purpose, which uses the change in resistance of an interdigital electrode structure due to soot deposition to detect the soot. Based on its functionality, the resistive soot sensor is classified according to the collecting principles. Such soot sensors are, for example, known from published German patent application document DE 101 49 333 A1 or published international patent application document WO 2003/006976 A2.

In such resistive particle sensors for conductive particles, two or more metallic electrodes are formed on an electrically insulating substrate, the particles, in particular sooty particles which accumulate under the effect of a measuring voltage, short-circuiting the comb-like meshed electrodes, and a decreasing resistance or an increasing current being measurable between the sensor electrodes at a constant applied voltage. To regenerate the sensor element after soot has accumulated, the sensor element is burned clean with the aid of an integrated heating element. The evaluation of the sensor signal is carried out in the system by comparing the setpoint trigger time ascertained from a signal behavior model, taking into account the raw emission model and the actual sensor trigger time.

In order to monitor the functionality of the electrodes and thus of the sensor in the field, a measuring voltage is applied to the electrodes at the end of the regeneration. As a result, an ion stream is created, which is caused mostly by impurities in the form of sodium. If the ion stream exceeds a certain threshold value, the electrodes are to be considered to be intact.

Despite the numerous advantages of the method and device for detecting particles which are known from the related art, they still have potential for improvement. Thus, the above-described form of self-diagnosis is resistant to aging only to a limited extent. Up to now, the intrinsic conductivity of the electrode measuring cell has generally been measured once at a certain temperature. However, the aging of the sensor is generally associated with a drop in the self-diagnosis current. Thus, after the sensor has aged for a certain period of time, the self-diagnosis current may fall below the threshold value without this being attributed to a defect of the sensor. A sensor in which a current smaller than 2 µA is measured has, for example, previously been regarded in many cases as a reject, since currents up to 1.5 µA may be attributed to shunts. Thus, after a certain period of aging, it is no longer possible to differentiate whether the undershooting of the threshold value is caused by aging or by a defect.

BRIEF SUMMARY OF THE INVENTION

Therefore, a method for checking the function of a sensor for detecting particles, in particular soot, and a sensor for detecting particles, in particular soot, are provided, which at least largely avoid the disadvantages of known methods and devices and in which, for example, shunts may be eliminated as offsets.

The method according to the present invention for checking the function of a sensor for detecting particles, in particular soot, the sensor including at least two measuring electrodes which are situated on a substrate made of an electrically insulating material, and a heating element, includes the following steps, preferably in the following sequence:

carrying out a first current-voltage measurement at a first temperature to ascertain a first measured variable, carrying out a second current-voltage measurement at a second temperature to ascertain a second measured variable, and forming a difference between the first measured variable and the second measured variable.

The second current-voltage measurement may, for example, be carried out conditionally or unconditionally. The second current-voltage measurement may thus, for example, be carried out only if a predefined condition has been met, for example, a condition which is checked after the first current-voltage measurement has been carried out. For example, the second current-voltage measurement may be carried out only if the first measured variable reaches and/or falls below a threshold value.

The second temperature may be lower than the first temperature. The second temperature may be 80° C. to 220° C., preferably 100° C. to 200° C., and even more preferably 120° C. to 180° C. lower than the first temperature, for example, 150° C. The second current-voltage measurement may be carried out chronologically after the first current-voltage measurement. The second current-voltage measurement may, for example, be carried out 0.5 s to 20.0 s after the first current-voltage measurement. Preferably, the second current-voltage measurement may be carried out 1.0 s to 20.0 s, preferably 1.0 s to 15 s, and even more preferably from 1.0 to 12 s chronologically after the first current-voltage measurement, for example, within 10 s after the first current-voltage measurement.

The first current-voltage measurement and/or the second current-voltage measurement may each be carried out over a period from 100 ms to 500 ms, preferably from 200 ms to 400 ms, and even more preferably from 250 ms to 350 ms, for example, 300 ms.

The first current-voltage measurement and/or the second current-voltage measurement may each be carried out once or repeatedly. The above-described difference may, for example, be formed between measured variables which have been ascertained from chronologically contiguous current-voltage measurements, or between measured variables which have been ascertained from chronologically noncontiguous current-voltage measurements.

In particular, a difference between the first measured variable and the second measured variable from 0.10 µA to 0.60 µA, preferably from 0.15 µA to 0.35 µA, and even more preferably from 0.20 µA to 0.30 µA, for example, 0.25 µA, may be established as a threshold value for a determination of the functional capability of the sensor. The first temperature may be kept essentially constant over a period from 20 s to 80 s, preferably from 30 s to 60 s, and even more preferably from 40 s to 50 s, for example, 45 s, the first current-voltage measurement being measured at the end of the period. A threshold value for the first measured variable may be a current from 1.5 µA to 2.5 µA and preferably from 1.7 µA to 2.3 µA and even more preferably from 1.8 µA to 2.2 µA, for example, 2.0 µA. The first temperature may be from 700° C. to 860° C., preferably from 740° C. to 820° C., and even more preferably from 760° C. to 800° C., for example, 785° C., the second temperature being from 560° C. to 700° C., preferably from 600° C. to 660° C., and even more preferably from 620° C. to 640° C., for example, 635° C. The current-voltage measurement may include a measuring voltage from 7.0 V to 10.0 V and preferably from 7.5 V to 9.0 V, for example, 8.5 V.

A sensor according to the present invention for detecting particles, in particular soot in an exhaust gas flow in an internal combustion engine, may include at least two measuring electrodes which are situated on a substrate made of an electrically insulating material, a heating element, and a controller, the controller being configured to carry out a method as recited in one of the preceding claims.

The measuring electrodes may in particular be designed as interdigital electrodes, i.e., as meshed measuring electrodes, for example, two or more meshed comb structures.

Within the scope of the present invention, particles are to be understood in particular to be electrically conductive particles, for example, soot or dust.

Within the scope of the present invention, measuring electrodes are to be understood to be electrodes which are suitable for measuring a current or a voltage.

Within the scope of the present invention, an electrically insulating material is to be understood to be any material which is suitable for preventing a current flow, for example, a ceramic.

Within the scope of the present invention, a current-voltage measurement is to be understood to be a measurement in which either a certain voltage is applied to the measuring electrodes and a current flow is measured between the measuring electrodes, or a current is applied to the measuring electrodes and a voltage is measured between the measuring electrodes. A current-voltage measurement may in particular be a resistance measurement, a resistance of the structure formed by the measuring electrodes and the substrate being measurable. For example, a voltage-controlled or voltage-regulated measurement and/or a current-controlled and/or current-regulated measurement may be carried out. The application of the current and/or the voltage may be carried out in the form of a continuous signal and/or also in the form of a pulsed signal. Thus, for example, a DC voltage and/or a DC current may be applied and a current response or a voltage response may be detected. Alternatively, a pulsed voltage and/or a pulsed current may be applied and a current response or a voltage response may be detected.

Within the scope of the present invention, a measured variable is to be understood to be a variable ascertained by the current-voltage measurement, which may correspondingly be an electric current or a voltage. An electrical resistance derived from it may also be used as a measured variable.

Within the scope of the present invention, keeping a temperature essentially constant is to be understood to be keeping a temperature at a certain predefined value over a certain period of time, which includes a deviation of maximal 15° C. and preferably maximal 5° C.

Within the scope of the present invention, carrying out a current-voltage measurement at the end of a period of time is to be understood to be carrying out the current-voltage measurement in such a way that the current-voltage measurement essentially ends simultaneously with the period of time, i.e., with a time offset of maximal 1 s.

Within the scope of the present invention, a controller is to be understood to be any device which is suitable for carrying out the method according to the present invention and for carrying out the corresponding control and/or regulation operations. The controller may be an internal controller associated with the sensor or also part of a controller of an internal combustion engine, for example, part of an engine controller of an internal combustion engine, in particular of a diesel engine.

Within the scope of the present invention, interdigital electrodes are to be understood to be electrodes which are arranged in such a way that they mesh, in particular in a comb-shaped manner.

Thus, within the scope of the present invention, a change of the operating strategy and an adaptation of the software of the operating electronics of an internal combustion engine are provided, with which the lifetime of the electrode self-diagnostics may be improved significantly. In particular, by measuring the intrinsic conductivity of the electrode measurement cell twice at different temperatures and evaluating the difference, shunt offset currents may be eliminated and the evaluation limit may be reduced. In contrast to the related art described above, the difference between two current or voltage values will now be used as an evaluation criterion. By using a difference formation to be able to eliminate the shunts as offsets, the evaluation threshold for the functionality of the sensor may be significantly reduced, for example, to 0.25 µA. A sensor failure caused by aging of the sensors and a related reduction of the self-diagnosis current is thus delayed significantly.

DETAILED DESCRIPTION OF THE INVENTION

Figure 1:
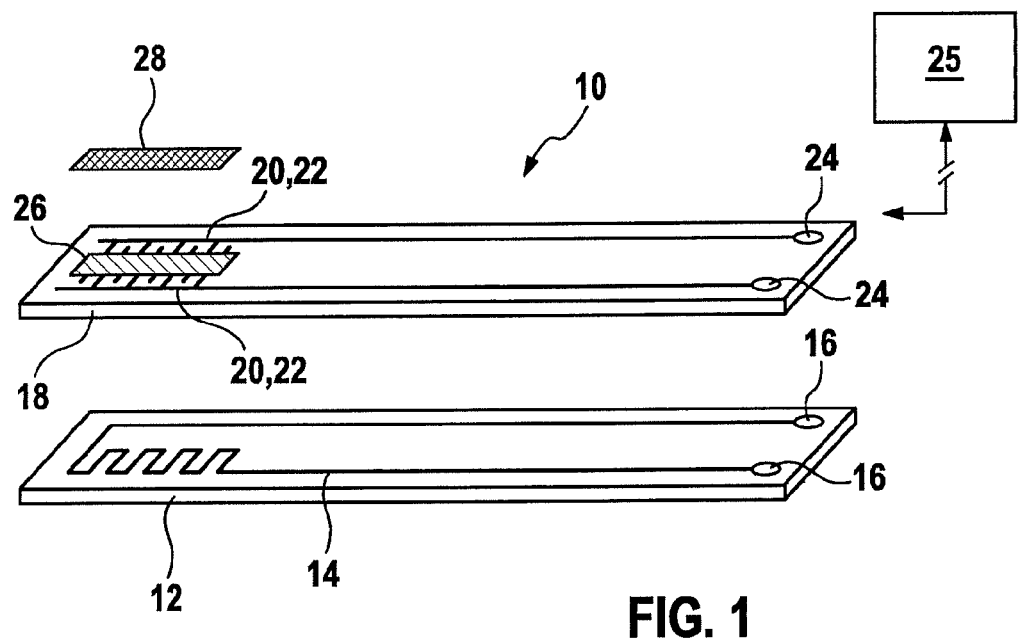
FIG. 1 shows an exploded view of a sensor for detecting particles.

FIG. 1 shows a sensor 10 for detecting particles, in particular soot, in a gas flow, for example, an exhaust gas flow of an internal combustion engine, which is used for installation in an exhaust gas system of a motor vehicle. For example, sensor 10 is designed as a soot sensor and is preferably situated downstream from a soot filter of a motor vehicle having a diesel internal combustion engine.

Sensor 10 includes a plate-shaped carrier layer 12 which is at least partially manufactured from an electrically insulating material, for example, a ceramic such as aluminum oxide. A heating element 14 is integrated into carrier layer 12 which is connectable to a suitable voltage source via contacts 16 and is used to burn sensor 10 clean of possibly accumulated particles such as sooty particles.

A plate-shaped substrate 18 is situated on carrier layer 12 which is manufactured at least partially from an electrically insulating material, for example, a ceramic such as aluminum oxide. A structure made up of two measuring electrodes 20 is situated on substrate 18. For example, measuring electrodes 20 are designed as interdigital electrodes 22 in such a way that they mesh in a comb-shaped manner. Measuring electrodes 20 are connectable to a controller 25 via contacts 24.

In the area in which measuring electrodes 20 mesh in a comb-shaped manner, measuring electrodes 20 may be at least partially covered by a dielectric 26, so that measuring electrodes 20 are able to be used as electrodes of a capacitor having a measurable capacitance. Dielectric 26 may in turn be provided with a protective layer 28, so that it is isolated with respect to the surrounding medium, thereby preventing a degeneration of dielectric 26.

Sensor 10 may furthermore include a housing which surrounds the structure depicted in FIG. 1 and which is not shown in FIG. 1 in order to simplify the explanation of the structure of sensor 10. For example, the housing may be designed as a catching sleeve which is provided with an opening in an area above measuring electrodes 20 and is used for calming a gas flow which is flowing in the exhaust gas system, so that sooty particles or other particles contained in the gas flow preferably accumulate in the area of measuring electrodes 20.

Sensor 10 according to FIG. 1 may work as follows. If soot or other electrically conductive particles accumulate on substrate 18, an electrical resistance between the two measuring electrodes 20 is reduced. By measuring the impedance between the two measuring electrodes 20, a behavior results which is typical for a so-called RC element. This means that the soot or particle concentration in the relevant exhaust gas may be determined using the chronological change of the resistance component of the RC element.

To regenerate sensor 10, the accumulated particles are burned off after a certain time with the aid of heating element 14 which is integrated into carrier layer 12. In a sensor 10 which is functioning properly, after this so-called bake-out, the resistance between measuring electrodes 20 should increase significantly and preferably approach infinity. Since the functioning of sensor 10 for the detection of the particle concentration is known per se, for example, from the aforementioned related art of WO 2003/006976 A2, more detailed reference will not be made at this point to the normal functioning of sensor 10, and the content of the aforementioned related art which relates to the description of the functionality of sensor 10 is fully included by reference herein. Instead, the method according to the present invention for checking the function of sensor 10 will now be described. The method may, for example, be carried out by aforementioned controller 25. In particular, the method is described on the basis of FIG. 2.

Figure 2:
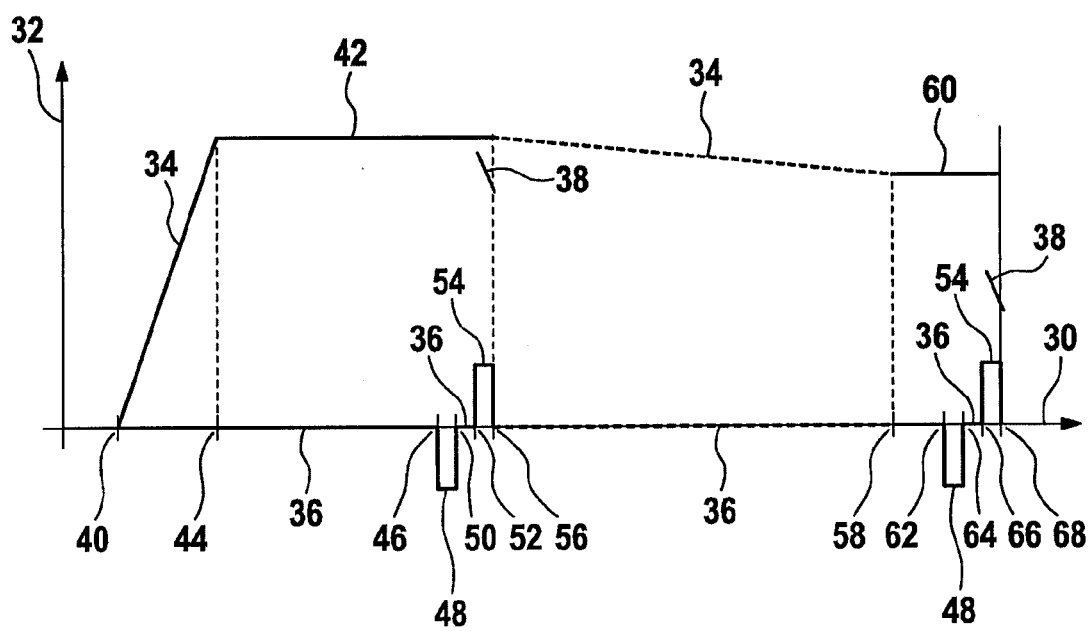
FIG. 2 shows a time diagram of the method according to the present invention.

In particular, in FIG. 2, time is depicted on x-axis 30, and the profile of certain variables, such as a temperature 34, a voltage 36, and an electric current 38, is depicted over time on y-axis 32. FIG. 2 shows, for example, the above-described burning clean or bake-out of sensor 10. For this purpose, sensor 10 is heated with the aid of heating element 14, as is apparent, for example, based on temperature profile 34 starting at a first point in time 40. Sensor 10 is heated until it reaches a first temperature 42 at a second point in time 44. First temperature 42 is kept essentially constant starting at second point in time 44 over a period from 20 s to 80 s, preferably 30 s to 60 s, and even more preferably 40 s to 50 s, for example, 45 s. First temperature 42 may be, for example, from 700° C. to 860° C., preferably from 740° C. to 820° C., and even more preferably from 760° C. to 800° C., for example, 785° C.

Furthermore, FIG. 2 shows the profile of voltage 36 applied to measuring electrodes 20. As is apparent from FIG. 2, the voltage between first point in time 40 and second point in time 44 is constantly 0 V. At a third point in time 46, a negative voltage 48 from −7.5 V to −9.0 V is applied to measuring electrodes 20, for example, −8.5 V, which is used for a reversal of polarity due to the charge carriers of the ceramic of substrate 18. Negative voltage 48 is kept constant up to a fourth point in time 50. The period between third point in time 46 and fourth point in time 50 is, for example, 300 ms. Between fourth point in time 50 and a fifth point in time 52 following shortly thereafter, voltage 36 of 0 V is again present.

Starting at fifth point in time 52, a first current-voltage measurement is carried out for ascertaining a first measured variable. In this exemplary embodiment, the current-voltage measurement is carried out in such a way that a constant measuring voltage 54 is applied to measuring electrodes 20 and electric current 38 flowing between measuring electrodes 20 is ascertained as a measured variable. However, it is alternatively possible to apply a measuring current to measuring electrodes 20 and to measure the voltage. Measuring voltage 54 may be from 7.0 V to 10.0 V and preferably from 7.5 V to 9.0 V, for example, 8.5 V. The first current-voltage measurement is carried out at first temperature 42 at a sixth point in time 56. Starting at sixth point in time 56, a voltage 36 of 0 V is again present at the measuring electrodes. In other words, the first current-voltage measurement is carried out at the end of the period, over which first temperature 42 is kept constant. The period between fifth point in time 52 and sixth point in time 56, over which the first current-voltage measurement is carried out, may be carried out from 100 ms to 500 ms, preferably from 200 ms to 400 ms, and even more preferably from 250 ms to 350 ms, for example, 300 ms. FIG. 2 shows that during the application of measuring voltage 54, current 38 is detected as a first measured variable having a falling shape due to a migration of charge carriers. The time-averaged current value over the period of the first current-voltage measurement may therefore be used as a first measured variable.

If the first measured variable in the form of electric current 38 exceeds a threshold value of first measured variable from 1.5 µA to 2.4 µA and preferably from 1.7 µA to 2.3 µA and even more preferably from 1.8 µA to 2.2 µA, for example, 2.0 µA, this already indicates the functionality of sensor 10. In this case, additional measurements are not mandatory. If the first measured variable falls below the threshold value for the first measured variable, the method according to the present invention is continued. For this purpose, between sixth point in time 56 and a seventh point in time 58, temperature 34 is lowered significantly to a second temperature 60. Second temperature 60 is, for example, from 80° C. to 220° C., preferably from 100° C. to 200° C., and even more preferably from 120° C. to 180° C. lower than first temperature 42, for example, 150° C. lower than first temperature 42. For example, second temperature 58 is from 560° C. to 700° C., preferably from 600° C. to 660° C., and even more preferably from 620° C. to 640° C., for example, 635° C. Second temperature 60 is likewise kept constant starting at seventh point in time 58.

At an eighth point in time 62, negative voltage 48 of −8.5 V is in turn applied to measuring electrodes 20, which is used for a reversal of polarity due to the charge carriers of the ceramic of substrate 18. Negative voltage 48 is kept constant up to a ninth point in time 64. The period between eighth point in time 62 and ninth point in time 64 is, for example, 300 ms. Between ninth point in time 64 and a tenth point in time 66 following shortly thereafter, voltage 36 of 0 V is again present.

Starting at tenth point in time 66, a second current-voltage measurement is carried out for ascertaining a second measured variable. In this exemplary embodiment, the second current-voltage measurement is carried out similarly to the first current-voltage measurement in such a way that constant measuring voltage 54 of 8.5 V is applied to measuring electrodes 20 and electric current 38 flowing between measuring electrodes 20 is ascertained as a second measured variable. However, the second current-voltage measurement is carried out at second temperature 60 up to an eleventh point in time 68. The period between the tenth point in time 66 and the eleventh point in time 68, over which the second current-voltage measurement is carried out, may be carried out from 100 ms to 500 ms, preferably from 200 ms to 400 ms, and even more preferably from 250 ms to 350 ms, for example, 300 ms. FIG. 2 shows that during the application of measuring voltage 54, current 38 is detected as a second measured variable having a falling shape due to a migration of charge carriers. The current value which is averaged over time over the period of the second current-voltage measurement may therefore be used as a second measured variable. Due to the decreasing conductivity with falling temperature, current 38 during the second current-voltage measurement is lower than current 38 during the first current-voltage measurement.

The period for the measurement of the second current-voltage measurement is identical to the period of the first current-voltage measurement. The second current-voltage measurement is carried out 1.0 s to 20.0 s, preferably from 1.0 s to 15 s, even more preferably from 1.0 s to 12 s chronologically after the first current-voltage measurement, for example, within 10 s after the first current-voltage measurement. Among other things, the period is a function of the rate of cooling of sensor 10. After the second measured variable has been ascertained by the second current-voltage measurement, a difference is formed between the first measured variable and the second measured variable, i.e., ascertained current value 38 of the second current-voltage measurement is subtracted from ascertained current value 38 of the first current-voltage measurement. As a basis of measurement, based on which a functionality of sensor 10 is inferred, a difference between the first measured variable and the second measured variable is then established using a threshold value, for example, from 0.10 µA to 0.60 µA, preferably from 0.15 µA to 0.35 µA, and even more preferably from 0.20 µA to 0.30 µA, for example, 0.25 µA.

If the threshold value is undershot, a defect of sensor 10 is inferred. If this threshold value is exceeded, the functionality of sensor 10 may be inferred. By forming the difference, shunts are eliminated as offsets. Accordingly, a failure of sensor 10 due to aging of sensor 10 and a related reduction of the diagnostic current occurs significantly later.

What is claimed is:

1. A method for checking for a fault of a sensor for detecting particles, wherein the sensor includes at least two measuring electrodes which are situated on a substrate made of an electrically insulating material, and a heating element, the method comprising:
   setting a temperature of the sensor to a first temperature for a predetermined period of time using the heating element to carry out a cleaning operation to burn off the particles from the sensor during the predetermined period of time;
   after carrying out the cleaning operation over the predetermined period of time, carrying out a first current-voltage measurement using the at least two measuring electrodes at the first temperature to ascertain a first measured current-voltage variable;
   after carrying out the first current-voltage measurement, setting the temperature of the sensor to a second temperature using the heating element;
   carrying out a second current-voltage measurement using the at least two measuring electrodes at the second temperature to ascertain a second measured current-voltage variable;
   forming a difference between the first measured current-voltage variable and the second measured current-voltage variable;
   comparing the formed difference to a predetermined threshold value; and
   determining a presence of the fault of the sensor based on the comparing.

2. The method as recited in claim 1, wherein the second current-voltage measurement is carried out conditional upon the first measured variable being below a second predetermined threshold value.

3. The method as recited in claim 1, wherein the second temperature is lower than the first temperature.

4. The method as recited in claim 1, wherein the second temperature is 100° C. to 200° C. lower than the first temperature.

5. The method as recited in claim 1, wherein the second current-voltage measurement is carried out chronologically after the first current-voltage measurement.

6. The method as recited in claim 1, wherein the second current-voltage measurement is carried out 1.0 second to 15.0 seconds after the first current-voltage measurement.

7. The method as recited in claim 1, wherein at least one of the first current-voltage measurement and the second current-voltage measurement is carried out over a period lasting between 200 ms to 400 ms.

8. The method as recited in claim 1, wherein a difference between the first measured variable and the second measured variable from 0.15 µA to 0.35 µA is established as a threshold value for a determination of the functional capability of the sensor.

9. The method as recited in claim 1, wherein the first temperature is kept essentially constant over the predetermined period which is from 30 seconds to 60 seconds, and the first current-voltage measurement is performed at the end of the period.

10. The method as recited in claim 2, wherein the second threshold value for the first measured variable is a current between 1.7 µA to 2.3 µA.

11. The method as recited in claim 1, wherein the first temperature is between 740° C. to 820° C., and the second temperature is between 600° C. to 660° C.

12. The method as recited in claim 1, wherein the current-voltage measurements include measuring voltages between 7.5 V to 9.0 V.

13. A sensor system for detecting particles in an exhaust gas flow of an internal combustion engine, the sensor system comprising:
- a sensor for detecting particles, including:
  - at least two measuring electrodes which are situated on a substrate made of an electrically insulating material; and
  - a heating element; and
- a controller including a processor configured to perform the following to check for a fault of the sensor:
  - setting a temperature of the sensor to a first temperature for a predetermined period of time using the heating element to carry out a cleaning operation to burn off the particles from the sensor during the predetermined period of time;
  - after carrying out the cleaning operation over the predetermined period of time, carrying out a first current-voltage measurement using the at least two measuring electrodes at the first temperature to ascertain a first measured current-voltage variable;
  - after carrying out the first current-voltage measurement, setting the temperature of the sensor to a second temperature using the heating element;
  - carrying out a second current-voltage measurement using the at least two measuring electrodes at the second temperature to ascertain a second measured current-voltage variable;
  - forming a difference between the first measured current-voltage variable and the second measured current-voltage variable;
  - comparing the formed difference to a predetermined threshold value; and
  - determining a presence of the fault of the sensor based on the comparing.

14. The sensor system as recited in claim 13, wherein the measuring electrodes are configured as interdigital electrodes.

15. The sensor system as recited in claim 13, wherein the second current-voltage measurement is carried out conditional upon the first measured variable being below a second predetermined threshold value.

16. The sensor system as recited in claim 13, wherein the presence of the fault of the sensor is determined conditional upon the formed difference being less than the predetermined threshold value.

17. The sensor system as recited in claim 13, wherein the second temperature is lower than the first temperature.

18. The method as recited in claim 1, wherein the presence of the fault of the sensor is determined conditional upon the formed difference being less than the predetermined threshold value.

19. The method as recited in claim 1, wherein a non-defective functionality status of the sensor is determined conditional upon the formed difference being greater than the predetermined threshold value.

20. The method as recited in claim 1, wherein a non-defective functionality status of the sensor is determined conditional upon determining that the first measured variable is greater than a second predetermined threshold value.

21. A non-transitory machine-readable storage medium having program instructions, which when executed by a processing device perform a method for checking for a fault of a sensor for detecting particles, the sensor including at least two measuring electrodes situated on a substrate made of an electrically insulating material and a heating element, the method comprising:
- setting a temperature of the sensor to a first temperature for a predetermined period of time using the heating element to carry out a cleaning operation to burn off the particles from the sensor during the predetermined period of time;
- after carrying out the cleaning operation over the predetermined period of time, carrying out a first current-voltage measurement using the at least two measuring electrodes at the first temperature to ascertain a first measured current-voltage variable;
- after carrying out the first current-voltage measurement, setting the temperature of the sensor to a second temperature using the heating element;
- carrying out a second current-voltage measurement using the at least two measuring electrodes at the second temperature to ascertain a second measured current-voltage variable;
- forming a difference between the first measured current-voltage variable and the second measured current-voltage variable;
- comparing the formed difference to a predetermined threshold value; and
- determining a presence of the fault of the sensor based on the comparing.

22. The non-transitory machine-readable storage medium as recited in claim 21, wherein the second current-voltage measurement is carried out conditional upon the first measured variable being below a second predetermined threshold value.

23. The non-transitory machine-readable storage medium as recited in claim 21, wherein the presence of the fault of the sensor is determined conditional upon the formed difference being less than the predetermined threshold value.

24. The non-transitory machine-readable storage medium as recited in claim 21, wherein the second temperature is lower than the first temperature.

25. The method as recited in claim 1, wherein the particles are sooty particles.

* * * * *